United States Patent
Li

(10) Patent No.: US 12,127,879 B2
(45) Date of Patent: Oct. 29, 2024

(54) ULTRASOUND IMAGING DEVICE AND METHOD FOR DETECTING PERISTALSIS OF ENDOMETRIUM

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/732,967

(22) Filed: Apr. 29, 2022

(65) Prior Publication Data

US 2023/0086624 A1    Mar. 23, 2023

Related U.S. Application Data

(63) Continuation of application No. PCT/CN2019/115773, filed on Nov. 5, 2019.

(51) Int. Cl.
  *A61B 8/08* (2006.01)
  *A61B 8/00* (2006.01)
  *A61B 8/14* (2006.01)

(52) U.S. Cl.
  CPC .............. *A61B 8/085* (2013.01); *A61B 8/463* (2013.01); *A61B 8/469* (2013.01); *A61B 8/5207* (2013.01);
  (Continued)

(58) Field of Classification Search
  CPC ......... A61B 8/085; A61B 8/463; A61B 8/469; A61B 8/5207; A61B 8/5223; A61B 8/54; A61B 8/56; A61B 8/14; G06T 7/00
  See application file for complete search history.

(56) References Cited

U.S. PATENT DOCUMENTS

2006/0106283 A1   5/2006  Wallace et al.
2013/0150718 A1   6/2013  Dixon et al.

FOREIGN PATENT DOCUMENTS

CN    108537785 A      9/2018
JP    2006263282 A  * 10/2006
WO  WO-2019053249 A1 *  3/2019  ........... A61B 5/4356

OTHER PUBLICATIONS

Kunz, G. et al., "The dynamics of rapid sperm transport through the female genital tract: evidence from vaginal sonography of uterine peristalsis and hysterosalpingoscintigraphy", (1996), Human Reproduction, vol. 11, No. 3, pp. 627-632 (Year: 1996).*

(Continued)

*Primary Examiner* — Baisakhi Roy
*Assistant Examiner* — Kaitlyn E Sebastian
(74) *Attorney, Agent, or Firm* — Sheppard Mullin Richter & Hampton LLP

(57) ABSTRACT

An ultrasonic imaging device and a method for detecting endometrial peristalsis. The method comprises: acquiring ultrasound echo data of the endometrium (1), and determining on said basis the peristaltic displacement or peristaltic speed of a point in the endometrium within a preset period of time (2); calculating peristalsis parameters of the endometrium according to the peristaltic displacement or the peristaltic speed of the point in the endometrium within the preset period of time, the peristalsis parameters being used to describe the moving state of endometrial peristalsis (3); and displaying the peristalsis parameters (4). Thus, peristalsis parameters are calculated automatically without relying on the subjective determination of an ultrasound doctor, which improves the accuracy and efficiency of the detection of peristalsis.

14 Claims, 6 Drawing Sheets

(52) U.S. Cl.
CPC .............. *A61B 8/5223* (2013.01); *A61B 8/54* (2013.01); *A61B 8/56* (2013.01); *A61B 8/14* (2013.01)

(56) References Cited

OTHER PUBLICATIONS

Meirzon et al. "A new method for analysis of non-pregnant uterine peristalsis using transvaginal ultrasound" (2011) Ultrasound Obstet Gynecol, vol. 38, pp. 217-224 (Year: 2011).*
PCT International Search Report and the Written Opinion mailed Aug. 11, 2020, issued in related International Application No. PCT/CN2019/115773, with partial English translation (9 pages).
D. Meirzon et al., "A new method for analysis of non-pregnant uterine peristalsis using transvaginal ultrasound", Ultrasound Obstet. Gynecol., vol. 38, Dec. 31, 2011, pp. 217-224.
PCT International Preliminary Report on Patentability mailed May 19, 2022, issued in related International Application No. PCT/CN2019/115773, with English translation (10 pages).
First Search dated May 1, 2023, issued in related Chinese Application No. 201980097843.9 (2 pages).
First Office Action dated May 7, 2023, issued in related Chinese Application No. 201980097843.9, with English machine translation (12 pages).

* cited by examiner

ULTRASOUND IMAGING DEVICE AND METHOD FOR DETECTING PERISTALSIS OF ENDOMETRIUM

CROSS-REFERENCE TO RELATED PATENT APPLICATION

This application is a continuation of International Patent Application No. PCT/CN2019/115773, filed with the China National Intellectual Property Administration (CNIPA) on Nov. 5, 2019. The content of the above application is incorporated herein by reference in its entirety.

TECHNICAL FIELD

The disclosure relates to the field of medical devices, and specifically to an ultrasound imaging device and a method for detecting endometrial peristalsis.

BACKGROUND

Clinically, it is found that peristalsis occurs in the endometrium, and that the peristalsis process changes with the growth of follicles and the ovulation process. Some clinical studies have shown that proper peristalsis can help transport sperm and provide nutrients and oxygen, while any peristalsis that is too moderate or too intense may reduce the success rate of conception. Therefore, the frequency (e.g., N times/minute), amplitude, and direction of endometrial peristaltic waves in clinical practice can be used as reference indicators for determining endometrial receptivity, estimating the chance of successful conception, and evaluating the developmental status of embryos.

At present, the ultrasonic detection of endometrial peristalsis is mainly performed by transvaginal ultrasound (TVUS). A doctor observes real-time changes of a two-dimensional B-mode image for a period of time (e.g., 1 minute), or observes a stored B-mode image video of a specific time length, and then captures movement information of the endometrium with the naked eye, so as to determine the amplitude, frequency, direction, etc. of the peristaltic waves. Such a method relies on the doctor's subjective and qualitative determination, and different doctors may give different conclusions. In addition, complex or subtle peristaltic states can hardly be identified with the naked eye, which is detrimental to an accurate determination.

SUMMARY

The disclosure mainly provides an ultrasound imaging device and a method for detecting endometrial peristalsis.

An embodiment provides a method for detecting endometrial peristalsis, the method including:
transmitting a first ultrasound wave to an endometrium, and receiving echoes of the first ultrasound wave to obtain first ultrasound echo data;
obtaining an ultrasound image of the endometrium based on the first ultrasound echo data;
determining a region of interest based on the ultrasound image;
transmitting a second ultrasound wave to a biological tissue corresponding to the region of interest, and receiving echoes of the second ultrasound wave to obtain second ultrasound echo data;
determining a peristaltic displacement or a peristaltic velocity of a point in the region of interest within a preset time length based on the second ultrasound echo data;
calculating a peristaltic parameter of the endometrium based on the peristaltic displacement or the peristaltic velocity of the point in the region of interest within the preset time length, where the peristaltic parameter is used to describe a motion status of the endometrial peristalsis; and
displaying the peristaltic parameter.

An embodiment provides a method for detecting endometrial peristalsis, the method including:
transmitting an ultrasound wave to an endometrium, and receiving echoes of the ultrasound wave to obtain ultrasound echo data;
obtaining an ultrasound image of the endometrium based on the ultrasound echo data;
determining a peristaltic displacement or a peristaltic velocity of a point in the endometrium within a preset time length based on the ultrasound echo data;
calculating a peristaltic parameter of the endometrium based on the peristaltic displacement or the peristaltic velocity of the point in the endometrium within the preset time length, where the peristaltic parameter is used to describe a motion status of the endometrial peristalsis; and
displaying the peristaltic parameter.

An embodiment provides a method for detecting endometrial peristalsis, the method including:
obtaining ultrasound echo data from an endometrium;
determining a peristaltic displacement or a peristaltic velocity of a point in the endometrium within a preset time length based on the ultrasound echo data;
calculating a peristaltic parameter of the endometrium based on the peristaltic displacement or the peristaltic velocity of the point in the endometrium within the preset time length, where the peristaltic parameter is used to describe a motion status of the endometrial peristalsis; and
displaying the peristaltic parameter.

An embodiment provides a method for detecting biological tissue peristalsis, the method including:
obtaining ultrasound echo data from a peristaltic object;
determining a peristaltic displacement or a peristaltic velocity of a point in the peristaltic object within a preset time length based on the ultrasound echo data;
calculating a peristaltic parameter of the peristaltic object based on the peristaltic displacement or the peristaltic velocity of the point in the peristaltic object within the preset time length, where the peristaltic parameter is used to describe a motion status of peristalsis of the peristaltic object; and
displaying the peristaltic parameter.

An embodiment provides a method for detecting endometrial peristalsis, the method including:
transmitting a first ultrasound wave to an endometrium, and receiving echoes of the first ultrasound wave to obtain first ultrasound echo data;
obtaining an ultrasound image of the endometrium based on the first ultrasound echo data;
determining a region of interest based on the ultrasound image;
transmitting a second ultrasound wave to a biological tissue corresponding to the region of interest, and receiving echoes of the second ultrasound wave to obtain second ultrasound echo data;

determining a peristaltic displacement or a peristaltic velocity of the endometrium in the region of interest based on the second ultrasound echo data; and displaying the peristaltic displacement or the peristaltic velocity.

An embodiment provides a method for detecting endometrial peristalsis, the method including:

transmitting an ultrasound wave to an endometrium, and receiving echoes of the ultrasound wave to obtain ultrasound echo data;

obtaining an ultrasound image of the endometrium based on the ultrasound echo data;

determining a peristaltic displacement or a peristaltic velocity of the endometrium based on the ultrasound echo data; and displaying the peristaltic displacement or the peristaltic velocity.

An embodiment provides a method for detecting endometrial peristalsis, the method including:

obtaining ultrasound echo data from an endometrium;

determining a peristaltic displacement or a peristaltic velocity of the endometrium based on the ultrasound echo data; and displaying the peristaltic displacement or the peristaltic velocity.

An embodiment provides a method for detecting biological tissue peristalsis, the method including:

transmitting a first ultrasound wave to a peristaltic object, and receiving echoes of the first ultrasound wave to obtain first ultrasound echo data;

obtaining an ultrasound image of the peristaltic object based on the first ultrasound echo data;

determining a region of interest based on the ultrasound image;

transmitting a second ultrasound wave to a biological tissue corresponding to the region of interest, and receiving echoes of the second ultrasound wave to obtain second ultrasound echo data;

determining a peristaltic displacement or a peristaltic velocity of the peristaltic object in the region of interest based on the second ultrasound echo data; and displaying the peristaltic displacement or the peristaltic velocity.

An embodiment provides a method for detecting biological tissue peristalsis, the method including:

transmitting an ultrasound wave to a peristaltic object, and receiving echoes of the ultrasound wave to obtain ultrasound echo data;

obtaining an ultrasound image of the peristaltic object based on the ultrasound echo data;

determining a peristaltic displacement or a peristaltic velocity of the peristaltic object based on the ultrasound echo data; and displaying the peristaltic displacement or the peristaltic velocity.

An embodiment provides an ultrasound imaging device, including:

an ultrasound probe configured to transmit an ultrasound wave to a region of interest in a biological tissue, and receive echoes of the ultrasound wave;

a transmitter/receiver circuit configured to control the ultrasound probe to transmit an ultrasound wave to an endometrium, and receive echoes of the ultrasound wave to obtain ultrasound echo data;

a human-machine interaction apparatus configured to receive a user's input and output visual information; and a processor configured to obtain an ultrasound image of the endometrium based on the ultrasound echo data; determine a peristaltic displacement or a peristaltic velocity of a point in the endometrium within a preset time length based on the ultrasound echo data; calculate a peristaltic parameter of the endometrium based on the peristaltic displacement or the peristaltic velocity of the point in the endometrium within the preset time length, where the peristaltic parameter is used to describe a motion status of the endometrial peristalsis; and display the peristaltic parameter using the human-machine interaction apparatus.

An embodiment provides an ultrasound imaging device, including:

a memory configured to store a program; and a processor configured to execute the program stored in the memory to implement a method as described above.

An embodiment provides a computer-readable storage medium including a program, where the program is executable by a processor to implement a method as described above.

Beneficial Effects

According to the ultrasound imaging device and the method for detecting endometrial peristalsis in the foregoing embodiments, the ultrasound echo data from the endometrium is obtained, and the peristaltic displacement or the peristaltic velocity of the point in the endometrium within the preset time length is determined based on the ultrasound echo data; the peristaltic parameter of the endometrium is calculated based on the peristaltic displacement or the peristaltic velocity of the point in the endometrium within the preset time length, where the peristaltic parameter is used to describe the motion status of the endometrial peristalsis; and the peristaltic parameter is displayed. This implements automatic calculation of the peristaltic parameter, without relying on the subjective determination of a sonographer, thereby improving the accuracy and efficiency of peristalsis detection.

DESCRIPTION OF THE PREFERRED EMBODIMENTS

Figure 1:
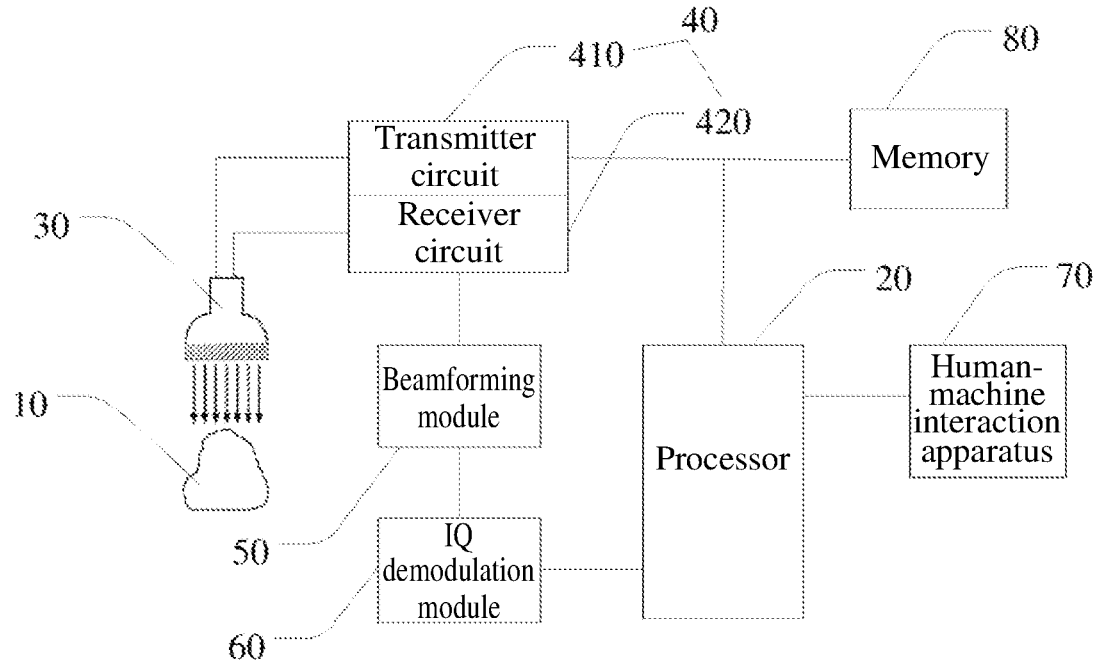
FIG. 1 is a structural block diagram of an ultrasound imaging device according to the disclosure.

The disclosure will be further described in detail below through specific implementations in conjunction with the accompanying drawings. Associated similar element reference numerals are used for similar elements in different implementations. In the following implementations, many details are described such that the disclosure may be better understood. However, it may be effortlessly appreciated by persons skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for persons skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. In addition, the steps or actions in the method description may also be exchanged or adjusted in order in a way that is obvious to persons skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish the described objects, and do not have any sequential or technical meaning. Moreover, as used in the disclosure, "connection" or "coupling", unless otherwise stated, includes both direct and indirect connections (couplings).

Peristalsis occurs in a plurality of organs or tissues, such as the intestinal tract, the stomach, and the endometrium, of the human body. In the disclosure, an ultrasound wave is continuously transmitted to these peristaltic organs or tissues for a period of time, and echoes thereof are detected; and a peristaltic displacement or a peristaltic velocity of the organs or tissues at different moments is calculated based on the echo data. In this way, an objective evaluation of a peristaltic state of the organs or tissues is made. A specific process will be described in detail below. In the following, measurement of peristaltic parameters of the endometrium is mainly taken as an example for description. However, those skilled in the art should understand that the disclosure is not limited to the endometrium. The methods and devices in the following embodiments are also applicable to measurement of peristaltic parameters of other tissues, such as the intestinal tract and the stomach. Herein, these peristaltic tissues to be subjected to measurement of peristaltic parameters are referred to as "peristaltic objects".

As shown in FIG. 1, an ultrasound imaging device provided in the disclosure includes an ultrasound probe 30, a transmitter/receiver circuit 40 (i.e., a transmitter circuit 410 and a receiver circuit 420), a beamforming module 50, an IQ demodulation module 60, a processor 20, a human-machine interaction apparatus 70, and a memory 80.

The ultrasound probe 30 includes a transducer (not shown) composed of a plurality of array elements arranged in an array. The plurality of array elements are arranged into a row to form a linear array or into a two-dimensional matrix to form an area array. Alternatively, the plurality of array elements may form a convex array. The array element is configured to transmit an ultrasound beam based on an excitation electrical signal, or convert a received ultrasound beam into an electrical signal. Therefore, each array element may be configured to implement mutual conversion of an electric pulse signal and an ultrasound beam, so as to transmit an ultrasound wave to an object to be imaged (a peristaltic object), or may be configured to receive echoes of the ultrasound wave that are reflected by a tissue. During ultrasound detection, the transmitter circuit 410 and the receiver circuit 420 may be used to control which array elements are used to transmit an ultrasound beam and which array elements are used to receive an ultrasound beam, or control the array elements to be used to transmit an ultrasound beam or receive echoes of the ultrasound beam in different slots. The array elements participating in transmission of the ultrasound wave can be simultaneously excited by the electrical signal, so as to simultaneously transmit the ultrasound wave; or the array elements participating in transmission of the ultrasound wave may be excited by several electrical signals having a specific time interval, so as to continuously transmit ultrasound waves having a specific time interval.

The array elements, for example, use piezoelectric crystals to convert an electrical signal into an ultrasound signal according to a transmitting sequence transmitted by the transmitter circuit 410. According to the use, the ultrasound signal may include one or more scanning pulses, one or more reference pulses, one or more driving pulses, and/or one or more Doppler pulses. According to the morphology of a wave, the ultrasound signal includes a focused wave and a plane wave.

A user moves the ultrasound probe 30 to find an appropriate position and angle to transmit an ultrasound wave to the peristaltic object, namely, the object 10 to be imaged and receive echoes of the ultrasound wave that are returned by the object 10 to be imaged, so as to output an analog ultrasound echo signal. The analog ultrasound echo signal is a channel analog electrical signal formed by using a receiving array element as a channel, and carries amplitude information, frequency information, and time information.

The transmitter circuit 410 is configured to generate a transmitting sequence under control of the processor 20. The transmitting sequence is used to control some or all of the plurality of array elements to transmit an ultrasound wave to a biological tissue. Parameters of the transmitting sequence include positions of the transmitting array elements, the number of the array elements, and transmission parameters of the ultrasound beam (such as amplitude, frequency, times of transmissions, transmission interval, transmission angle, waveform, and focusing position). In some cases, the transmitter circuit 410 is further configured to delay a phase of the transmitted beam, such that different transmitting array elements transmit ultrasound waves at different moments, and ultrasound beams transmitted can be focused in a predetermined region of interest. The parameters of the transmitting sequence may vary depending on different working modes, such as B image mode, C image mode, and D image mode (Doppler mode). After an echo signal is received by the receiver circuit 420 and processed by a subsequent module and corresponding algorithm, a B-mode image reflecting an anatomical structure of the tissue, a C-mode image reflecting the anatomical structure of the tissue and blood flow information, and a D-mode image reflecting a Doppler spectrum image may be generated.

The receiver circuit 420 is configured to receive ultrasound echo data from the ultrasound probe 30 and process the ultrasound echo data. The receiver circuit 420 may include one or more amplifiers, analog-to-digital converters (ADCs), etc. The amplifier is configured to amplify the received echo data after proper gain compensation. The amplifier is configured to sample the analog echo data at predetermined time intervals, so as to convert same into digitized data. The digitized echo data still retains amplitude information, frequency information, and phase information. Data output by the receiver circuit 420 may be output to the beamforming module 50 for processing, or output to the memory 80 for storage.

The beamforming module 50 is connected to the receiver circuit 420 using a signal, for corresponding beamforming processing such as delaying and weighted summation on the ultrasound echo data. Because an ultrasound wave receiving point in the detected tissue has different distances from receiving array elements, channel data of the same receiving point that is output by different receiving array elements have a delay difference, which needs to be processed through delaying. Phases are aligned, and the weighted summation is performed on different channel data at the same receiving point, to obtain the beamformed ultrasound echo data. The ultrasound echo data output by the beamforming module 50 is also referred to as radio frequency data (RF data). The beamforming module 50 outputs the radio frequency data to the IQ demodulation module 60. In some embodiments, alternatively, the beamforming module 50 may output the radio frequency data to the memory 80 for caching or storage, or directly output the radio frequency data to the processor 20 for image processing.

The beamforming module 50 may perform the above functions by hardware, firmware, or software. For example, the beamforming module 50 may include a central controller circuit (CPU), one or more microprocessors, or any other electronic component capable of processing input data according to specific logical instructions. When implemented by software, the beamforming module 50 may execute instructions stored on a tangible and non-transitory computer-readable medium (e.g., the memory) to perform beamforming calculation using any suitable beamforming method.

The IQ demodulation module 60 removes a signal carrier through IQ demodulation to extract tissue structure information contained in the data, and performs filtering to remove noise. A signal obtained at this time is referred to as a baseband signal (IQ data pair). The IQ demodulation module 60 outputs the IQ data pair to the processor 20 for image processing.

In some embodiments, alternatively, the IQ demodulation module 60 outputs the IQ data pair to the memory 80 for caching or storage, so that the processor 20 reads data from the memory 80 for subsequent image processing.

The IQ demodulation module 60 may also perform the above functions by hardware, firmware, or software. In some embodiments, the IQ demodulation module 60 may also be integrated with the beamforming module 50 in one chip.

The processor 20 is configured to be a central controller circuit (CPU), one or more microprocessors, a graphics controller circuit (GPU), or any other electronic component capable of processing input data according to specific logical instructions. The processor may control peripheral electronic components or read and/or store data from and/or to the memory 80 according to input instructions or predetermined instructions, or may process input data by executing a program in the memory 80. For example, one or more processing operations are performed on acquired ultrasound echo data in one or more working modes. The processing operations include, but are not limited to, adjusting or defining the form of an ultrasound wave emitted by the ultrasound probe 30 and generating various image frames for subsequent display on a display of the human-machine interaction apparatus 70, or adjusting or defining the content and form displayed on the display, or adjusting one or more image display settings (e.g., ultrasound image, interface component, locating a region of interest) displayed on the display.

When the echo data is received, the acquired ultrasound data may be processed by the processor 20 in real time during scanning or treatment, or may be temporarily stored on the memory 80 and processed in a near real-time manner during an online or offline operation.

In this embodiment, the processor 20 controls the operation of the transmitter circuit 410 and the receiver circuit 420, for example, controls the transmitter circuit 410 and the receiver circuit 420 to operate alternately or simultaneously. The processor 20 may further determine a suitable working mode according to the user's selection or the setting of the program, to generate a transmitting sequence corresponding to the current working mode, and send the transmitting sequence to the transmitter circuit 410, so that the transmitter circuit 410 uses the appropriate transmitting sequence to control the ultrasound probe 30 to transmit an ultrasound wave.

The processor 20 is further configured to process the ultrasound echo data to generate a grayscale image for signal strength variations within a scanning range. The grayscale image reflects an internal anatomical structure of the tissue, and is referred to as a B-mode image. The processor 20 may output the B-mode image to a display of the human-machine interaction apparatus 70 for display.

The human-machine interaction apparatus 70 is configured to perform human-machine interaction, that is, receive the user's input and output visual information. The human-machine interaction apparatus may receive the user's input using a keyboard, an operation button, a mouse, a trackball, etc., or using a touchscreen integrated with the display. The human-machine apparatus may output the visual information using the display.

Figure 2:
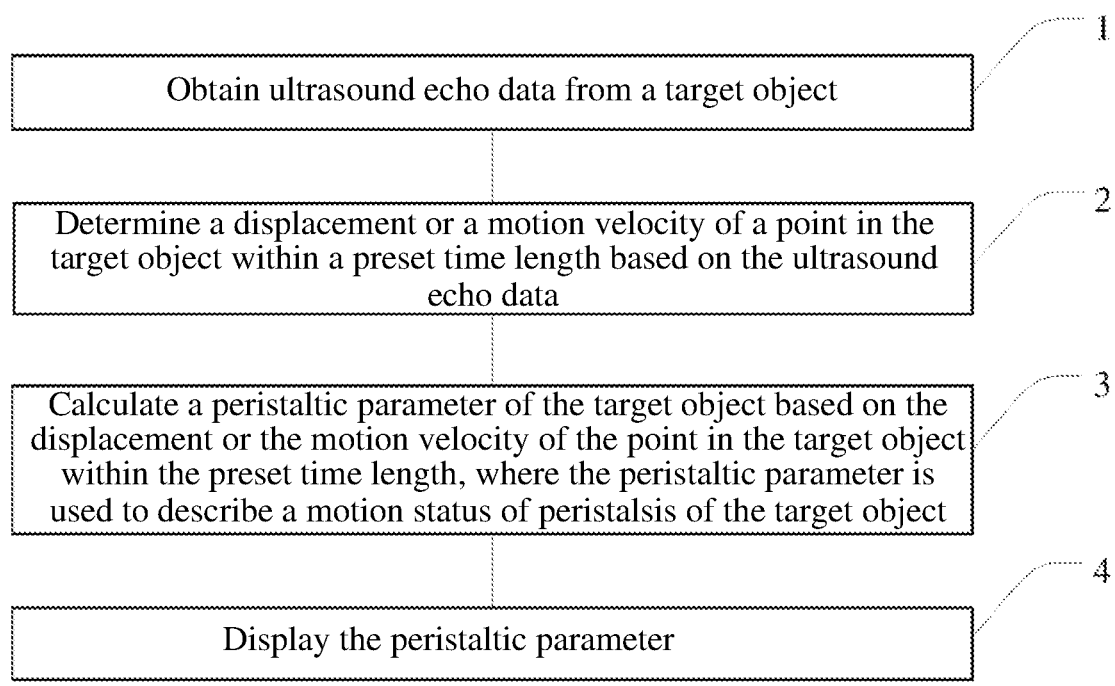
FIG. 2 is a flowchart of an embodiment of a method for detecting biological tissue peristalsis according to the disclosure.
Figure 3:
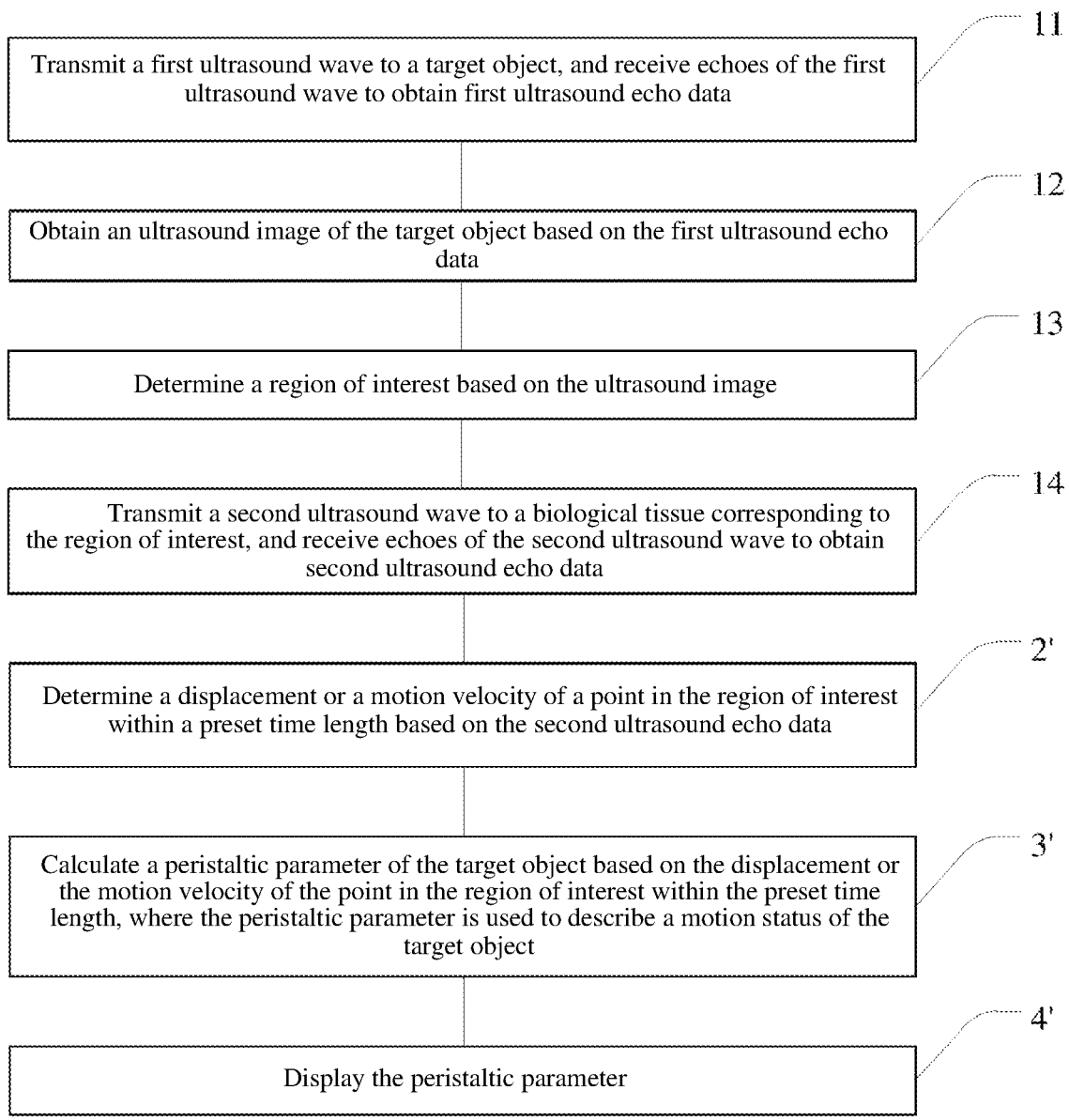
FIG. 3 is a flowchart of an embodiment of a method for detecting biological tissue peristalsis according to the disclosure.

Based on the ultrasound imaging device shown in FIG. 1, a method for detecting biological tissue peristalsis is shown in FIG. 2 and FIG. 3. The embodiment shown in FIG. 2 includes the following steps.

Step 1: The processor 20 obtains ultrasound echo data from the peristaltic object 10. The peristaltic object is a biological tissue capable of peristalsis, such as the intestinal tract, the stomach, or the endometrium. In this embodiment, the endometrium is taken as an example for description. As described above, the processing of an electrical signal obtained based on echoes of an ultrasound wave may include data processing steps such as analog signal gain compensation, beamforming, IQ demodulation, digital signal gain compensation, amplitude calculation, and image enhancement. The ultrasound echo data in the disclosure is data after the data processing on the electrical signal obtained based on the echoes of the ultrasound wave when the ultrasound probe scans the peristaltic object. In other words, the ultrasound echo data may be data generated in any one of the above-mentioned data processing steps. For example, the ultrasound echo data may be analog or digital ultrasound echo data before the beamforming, or may be data after the beamforming, such as data output by the beamforming module 50, or may be data after the IQ demodulation, such as data output by the IQ demodulation module 60, or may be ultrasound image data obtained by further processing based on the data after the beamforming or the data after the IQ demodulation. In other words, the ultrasound echo data for the peristaltic object may be obtained from the memory 80, or from the receiver circuit 420, the beamforming module 50, or the IQ demodulation module 60.

Step 2: The processor 20 determines a peristaltic displacement or a peristaltic velocity of a point in the endometrium within a preset time length based on the ultrasound echo data. The preset time length may be determined according to the user's input, or may be a default value of the ultrasound imaging device, or may be a scanning time length corresponding to the ultrasound echo data. An ultrasound wave is continuously transmitted to a target position in space for a period of time, and ultrasound echoes are received to obtain the ultrasound echo data. If the target position is moving, the ultrasound echo data obtained at different moments may be different. Based on a related method, a change amount or change rate of the ultrasound echo data at each moment can be measured, which is measurement of the peristaltic displacement or velocity.

Figure 4:
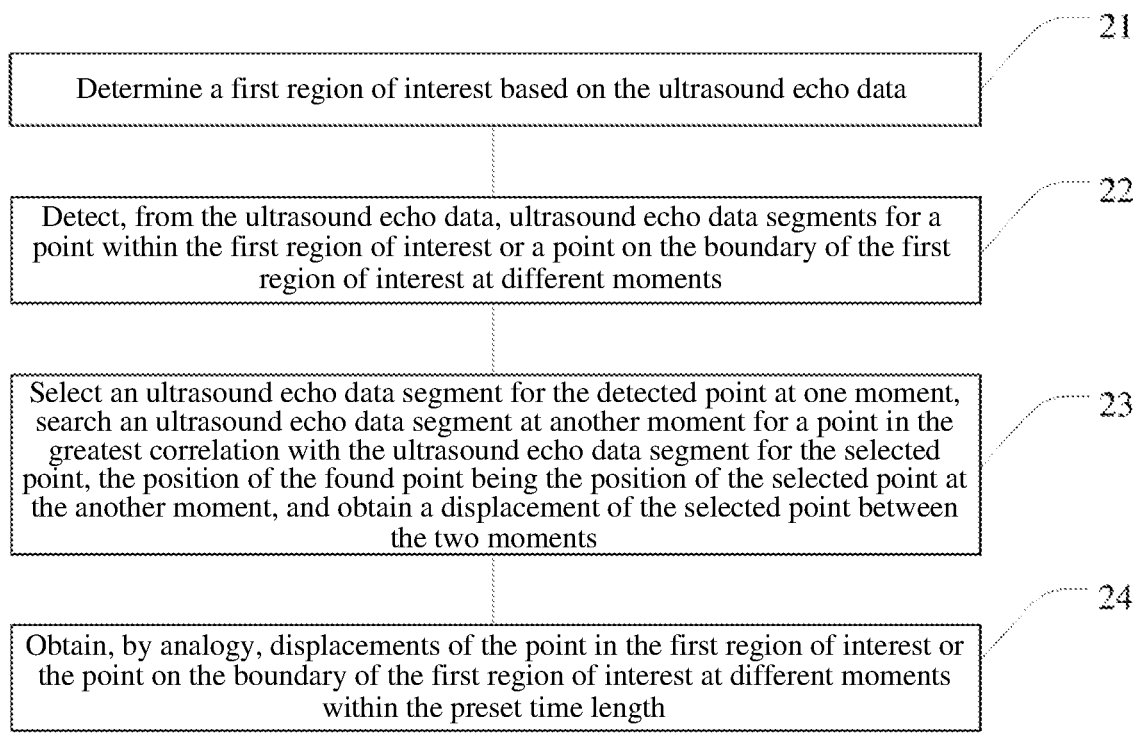
FIG. 4 is a flowchart of step 2 in FIG. 2.

There are a plurality of methods to measure the peristaltic displacement. For example, based on the idea of block-matching, for an ultrasound echo data segment at a position of the endometrium at a moment, ultrasound echo data segments at different positions at another moment are searched for a position in the greatest cross-correlation therewith. A difference between the position and the original position is the peristaltic displacement for the position between the two moments. Specifically, as shown in FIG. 4, the following steps are included.

Figure 5:
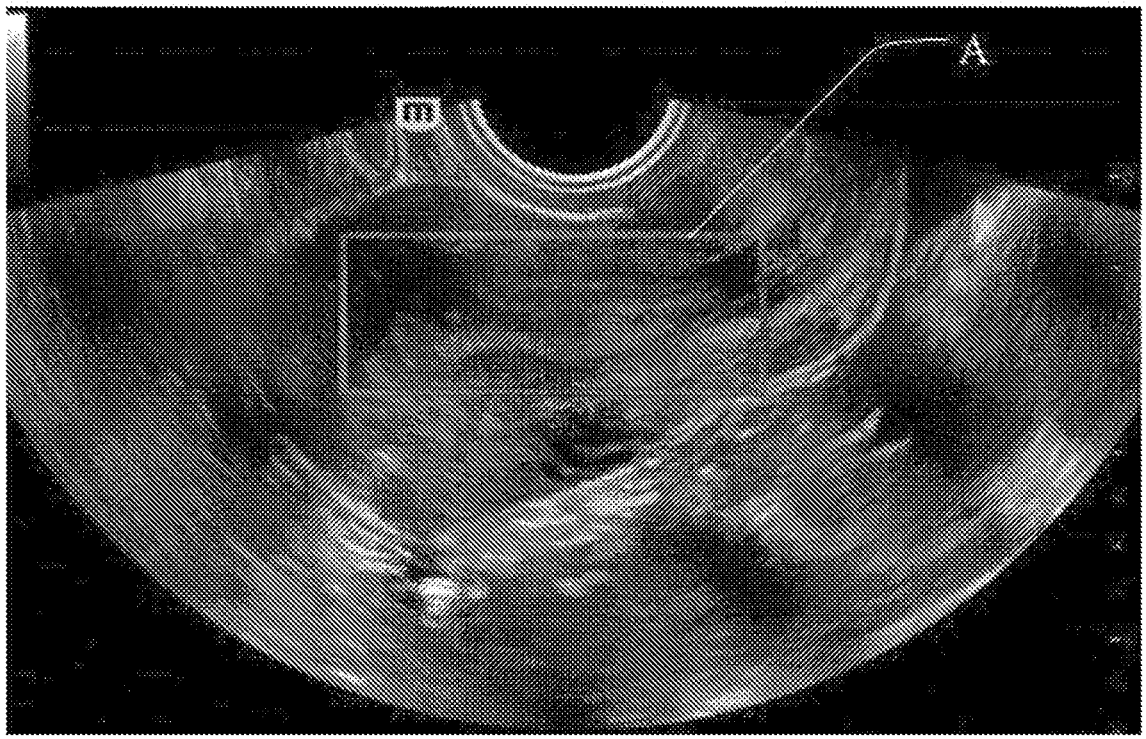
FIG. 5 is a schematic diagram of a region of interest in an ultrasound image.
Figure 6:
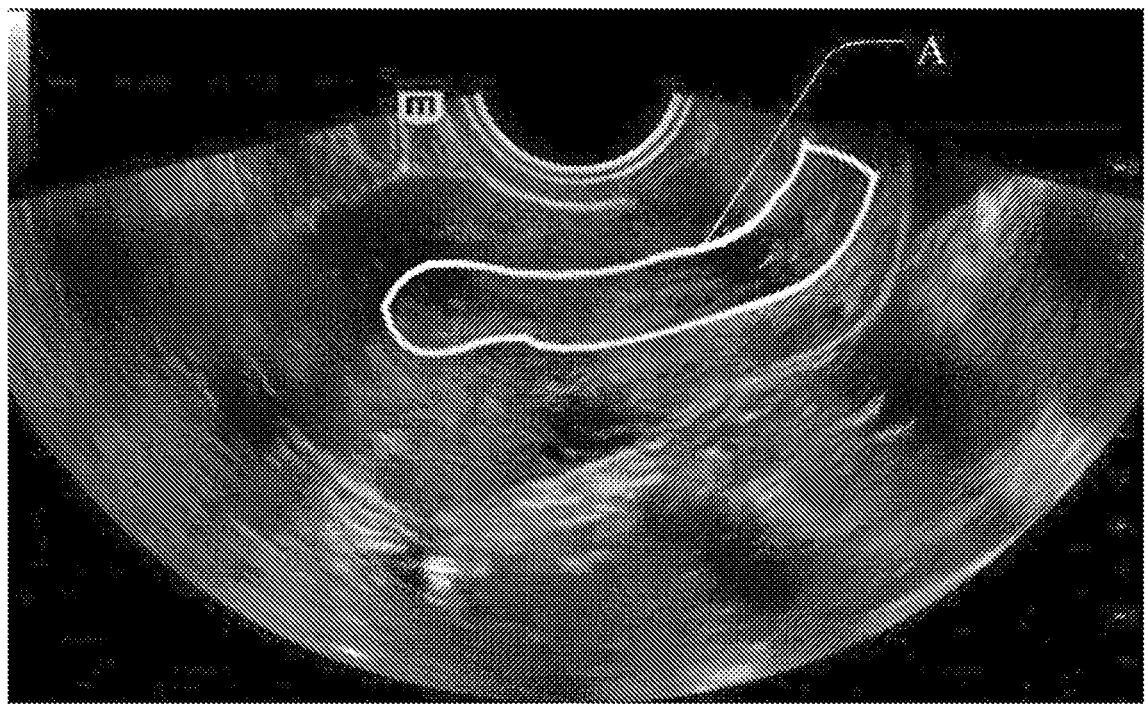
FIG. 6 is a schematic diagram of a region of interest in an ultrasound image.
Figure 9:
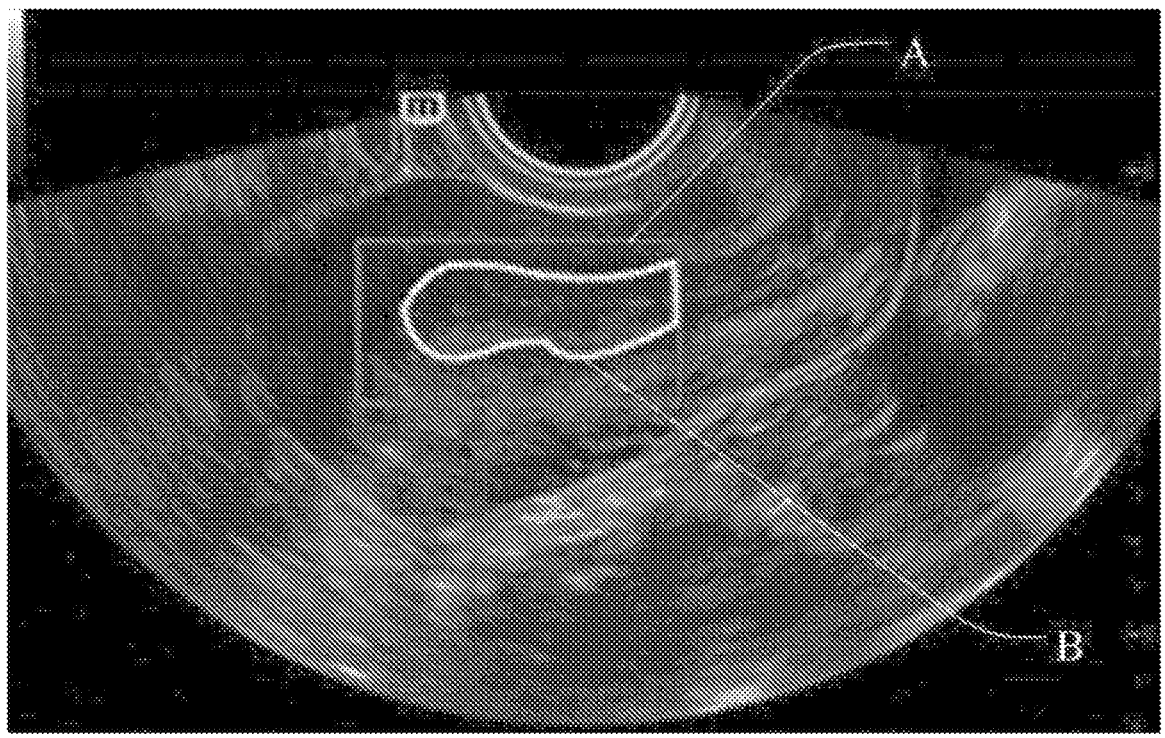
FIG. 9 is a schematic diagram of a region of interest in an ultrasound image.
Figure 10:
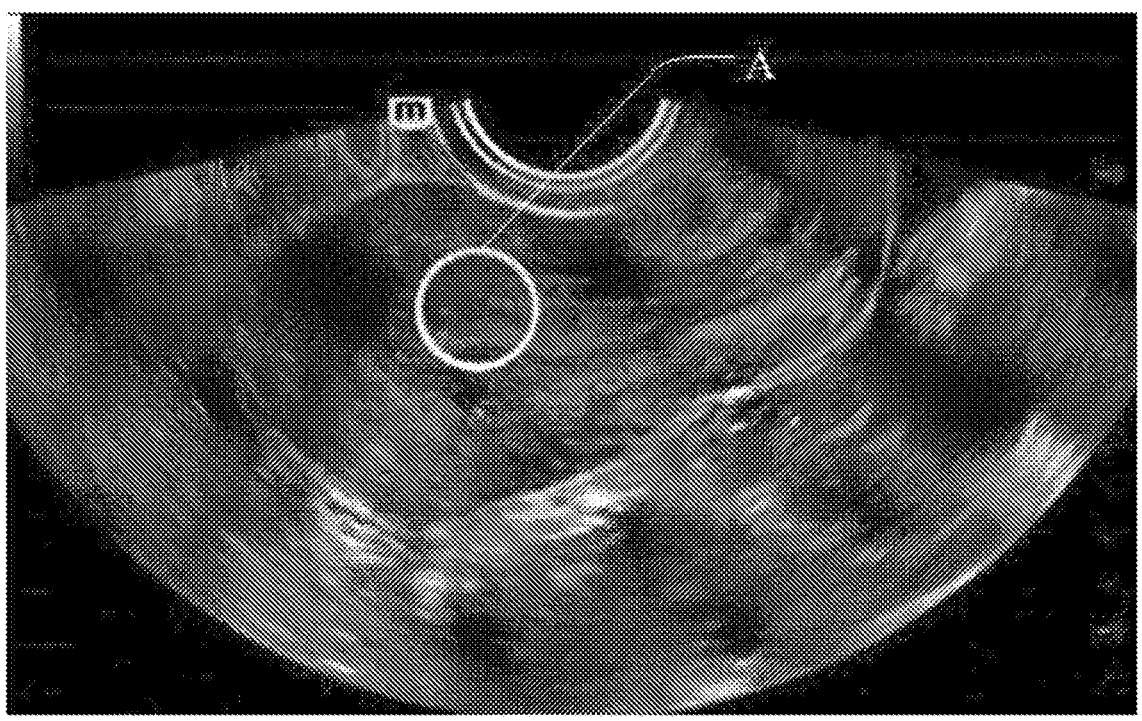
FIG. 10 is a schematic diagram of a region of interest in an ultrasound image.

Step 21: The processor 20 determines a first region of interest based on the ultrasound echo data. For example, the processor 20 generates an ultrasound image reflecting a section of the endometrium based on the ultrasound echo data. The ultrasound image may be moving or still. The ultrasound image may be an ultrasound B-mode image (as shown in FIG. 5 and FIG. 6), or may be a C-mode image or a three-dimensional ultrasound image. The processor 20 further displays the ultrasound image in a display interface of the human-machine interaction apparatus 70. The first region of interest is determined based on the ultrasound image. The first region of interest may be a region selected by the user using the human-machine interaction apparatus 70, or may be a region identified by the processor 20, for example, an identified endometrial region. In other words, the first region of interest may be determined in one of the following two manners. Manner 1: The human-machine interaction apparatus 70 receives a region selected by the user on the ultrasound image, and uses the selected region as the first region of interest, such as a region A in FIGS. 5, 8, 9, and 10. The user may select the entire endometrial region, or may select only a part of the endometrium as the first region of interest, which helps the user to perform targeted examination. Manner 2: The processor 20 performs image processing on the ultrasound image. For example, boundary recognition is performed by using an image segmentation technology to obtain the boundary of the endometrium. A region surrounded by the boundary of the endometrium is used as the first region of interest, such as a region A in FIG. 6 and a region B in FIG. 9. Certainly, step 21 is not mandatory. In an optional embodiment, this step may not be included, and all regions (the field of view of the ultrasound image) corresponding to the ultrasound echo data are directly processed subsequently.

Step 22: The processor 20 detects, from the ultrasound echo data, ultrasound echo data segments for a point within the first region of interest or a point on the boundary of the first region of interest at different moments. Specifically, when the first region of interest includes the endometrium and a region other than the endometrium, as shown in FIG. 5, the ultrasound echo data segments for the point within the first region of interest at different moments are detected. When the first region of interest is exactly the region surrounded by the boundary of the endometrium, as shown in FIG. 6, the ultrasound echo data segments for the point on the boundary of the endometrium at different moments are detected.

Step 23: Select an ultrasound echo data segment for the detected point at one moment, search an ultrasound echo data segment at another moment for a point in the greatest correlation (e.g., autocorrelation or cross-correlation) with the ultrasound echo data segment for the selected point, the position of the found point being the position of the selected point at the another moment, and obtain a peristaltic displacement of the selected point between the two moments.

Figure 7:
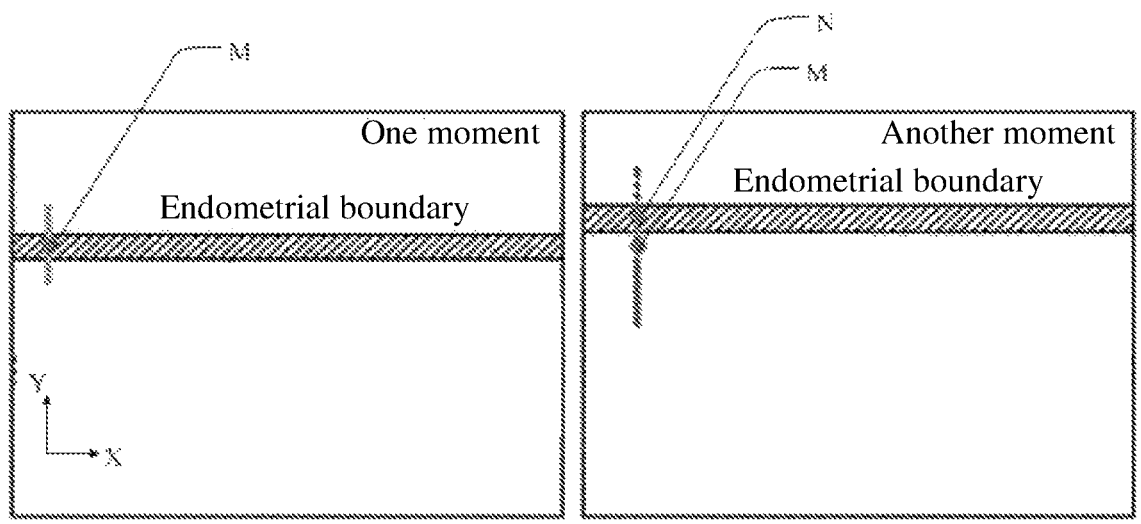
FIG. 7 is a schematic diagram of calculating peristaltic displacements of a point in a peristaltic object at different moments.
Figure 8:
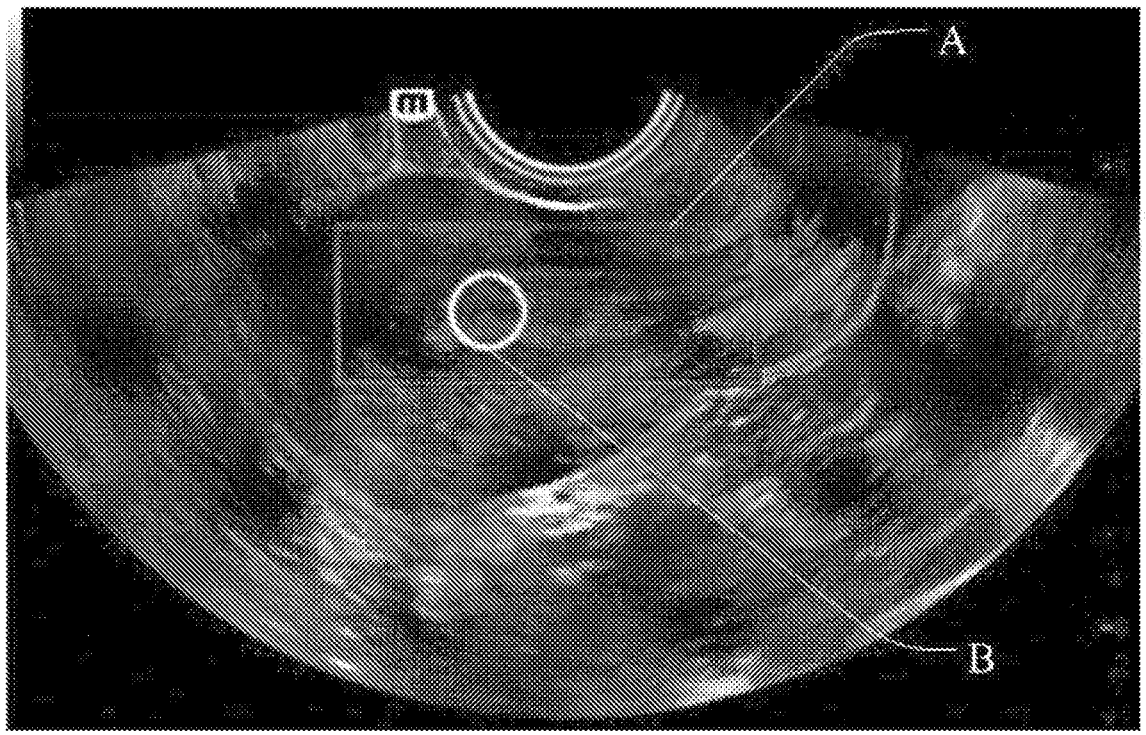
FIG. 8 is a schematic diagram of a region of interest in an ultrasound image.

For example, the detected point is a point on the endometrial boundary. As shown in FIG. 7, the processor 20 selects, from ultrasound echo data at one moment, a point on the endometrial boundary as the center point (the point M in the left part of FIG. 7), and takes a piece of one-dimensional data (the solid line segment passing through the point M in the left part of FIG. 7) of fixed size in the Y-axis direction (the thickness direction of the endometrium) of the ultrasound echo data at the moment, as characteristic information of the endometrial boundary at the position of the current selected point. The same position in ultrasound echo data at another moment is used as the center point (the point M in the right part of FIG. 7). A one-dimensional search region (the solid line segment in the right part of FIG. 7) in the Y-axis direction is searched for a data segment (the dashed line segment in the right part of FIG. 7) most matching the characteristic information, and the position of the center point (the point N in the right part of FIG. 7) of the data segment is used as the endometrial boundary at the current moment. The change of the position of each point between the two moments is the peristaltic displacement of the endometrial boundary between the two moments.

Step 24: Obtain, by analogy, peristaltic displacements of the point in the first region of interest or the point on the boundary of the first region of interest at different moments within the preset time length. The peristaltic displacement and the peristaltic velocity can be converted to each other according to d=v*t. To be specific, the peristaltic velocity can be obtained by calculating the first derivative of the peristaltic displacement with respect to time; and the acceleration can be obtained by calculating the second derivative of the peristaltic displacement with respect to time. Since the peristaltic displacement and the peristaltic velocity can be converted to each other by means of calculation, no emphasis and differentiation are made in the disclosure.

Certainly, in other embodiments, the peristaltic displacement and the peristaltic velocity can also be measured based on other peristaltic displacement measurement methods based on signal autocorrelation or cross-correlation. It is also possible to measure the peristaltic velocity of each point on the endometrial boundary at each moment based on the ultrasound Doppler effect and with a principle similar to that of conventional blood flow imaging.

Step 3: Calculate a peristaltic parameter of the endometrium based on the peristaltic displacement or the peristaltic velocity, obtained in step 2, of the point within the preset time length, where the peristaltic parameter is used to describe a motion status of the endometrial peristalsis. The peristaltic parameter may include at least one of amplitude of the peristalsis, frequency of the peristalsis, total significant peristaltic movement time within the preset time length, propagation direction of the peristaltic movement, propagation speed of the peristaltic movement, range of the peristaltic movement, and the like.

In an embodiment, alternatively, the peristaltic parameter here may be another parameter related to the peristaltic displacement or the peristaltic velocity that is calculated based on the peristaltic displacement or the peristaltic velocity and that reflects the motion status, for example, may be at least one of tissue strain caused by the peristalsis, tissue strain rate caused by the peristalsis, and acceleration of the peristaltic movement. In addition, in an embodiment, the peristaltic parameter here may also be at least one statistical quantity of the peristaltic displacement or the peristaltic velocity, for example, maximum peristaltic displacement, minimum peristaltic displacement, average peristaltic displacement, peristaltic displacement variance, maximum peristaltic velocity, minimum peristaltic velocity, average peristaltic velocity, or peristaltic velocity variance.

Peristalsis is usually regular and periodic, and propagates from a starting point of the endometrium to another position, similar to the propagation of a vibration wave. Therefore, a peristaltic wave is often used to describe peristalsis in the art. The specific peristaltic parameter above may be similar to a wave parameter. The preset time length may be a time length of main interest to clinical doctors, such as 1 minute or 30 seconds, but is usually greater than or equal to a period of the peristalsis to ensure that at least one complete peristalsis can be detected.

In some clinical situations, the peristalsis may also be irregular or disordered. Therefore, the peristaltic parameter above may also be a parameter reflecting the irregular or disordered state of the peristaltic movement, for example, degree of disorder in the peristaltic movement, degree of unevenness in the peristaltic amplitude, degree of unevenness in the peristaltic direction, and distribution of the peristaltic movement in the endometrium.

Similarly, in this step, specifically, the peristaltic parameter of the endometrium may be calculated directly based on the peristaltic displacement or the peristaltic velocity, obtained in step 2, of the point within the preset time length; or the peristaltic parameter of the endometrium may be calculated based on a peristaltic displacement or a peristaltic velocity of a point in a second region of interest within the preset time length. The second region of interest may be exactly the first region of interest, or may be a region within the first region of interest.

This embodiment is described by using an example in which the peristaltic parameter of the endometrium is calculated based on the peristaltic displacement or the peristaltic velocity of the point in the second region of interest within the preset time length. Similarly, the second region of interest may be a region selected by the user using the human-machine interaction apparatus 70, or may be a region identified by the processor 20, for example, an identified endometrial region. In other words, the second region of interest may be determined in one of the following two manners. Manner 1: The human-machine interaction apparatus 70 receives a region selected by the user on the ultrasound image, and uses the selected region as the second region of interest, such as a region B in FIG. 8. The user may select the entire endometrial region within the first region of interest, or may select only a part of the endometrium as the first region of interest, which helps the user to perform targeted examination. Manner 2: The processor 20 performs image processing on the first region of interest of the ultrasound image. For example, boundary recognition is performed by using an image segmentation technology to obtain the boundary of the endometrium. A region surrounded by the boundary of the endometrium is used as the second region of interest, such as a region B in FIG. 9.

The processor 20 generates a relationship curve of the peristaltic displacement versus time or a relationship curve of the peristaltic velocity versus time based on the peristaltic displacement or the peristaltic velocity of the point in the second region of interest within the preset time length. At least one of the amplitude of the peristalsis, the frequency of the peristalsis, and the total significant movement time within the preset time length is calculated based on the relationship curve. Taking the relationship curve of the peristaltic displacement versus time as an example, this curve is similar to a waveform diagram. From this curve, the period of the peristalsis can be obtained, and thus the frequency (times/min) of the peristalsis is obtained. The position of a peak or trough of the curve is the peristaltic amplitude of one peristalsis at the position corresponding to a single point. The maximum value of the peristaltic amplitudes at all points may be used as the peristaltic amplitude of the endometrium, or the average value of the peristaltic amplitudes of all points may be used as the peristaltic amplitude of the endometrium. It is compared whether the maximum peristaltic displacement of each peristalsis is greater than or equal to a preset value. The preset value is a threshold reflecting whether the peristalsis is significant, and may be an empirical value or a value set by the user. Time taken by all peristalses greater than or equal to the preset value is calculated to obtain the total significant movement time.

In an optional embodiment, the processor 20 may further calculate a motion parameter of the point based on the peristaltic displacement or the peristaltic velocity of the point in the second region of interest within the preset time length. The motion parameter includes at least one of maximum peristaltic displacement, minimum peristaltic displacement, average peristaltic displacement, and total significant movement time. The maximum peristaltic displacement is the maximum value of the peristaltic amplitude within the preset time length, the minimum peristaltic displacement is the minimum value of the peristaltic amplitude within the preset time length, and the average peristaltic displacement is the average value of the peristaltic amplitude within the preset time length. The motion parameter of each point is compared with a preset motion parameter to determine whether the motion parameter of each point reaches the preset motion parameter, and then the propagation direction of the peristalsis is obtained according to the order in which the points reach the preset motion parameter. The processor 20 is further configured to determine whether the motion parameter of each point exceeds a preset parameter threshold, where the parameter threshold may be the same as or different from the above-mentioned preset value. A region formed by points with the motion parameter exceeding the parameter threshold is used as the peristalsis range.

Further, after obtaining the propagation direction of the peristalsis, the processor 20 is further configured to select at least two points in the propagation direction, and obtain the propagation speed of the peristalsis based on a distance between the selected points in the propagation direction and a time difference between moments at which the selected points reach the preset motion parameter.

It can be seen that the peristalsis detection method provided in the disclosure can identify complex or subtle peristaltic states without relying on the doctor's subjective and qualitative determination.

Step 4: The processor 20 displays the peristaltic parameter using the human-machine interaction apparatus 70. For example, a value of the peristaltic parameter is displayed, such as a specific value of the amplitude of the peristalsis, the frequency of the peristalsis, the total significant movement time within the preset time length, or the propagation speed. Alternatively, a relationship curve of the amplitude of the peristalsis, the frequency of the peristalsis, the total significant movement time within the preset time length, or the propagation speed versus time may be displayed. Alternatively, a schematic diagram of the propagation direction or the peristalsis range may be displayed. The peristaltic parameter is displayed, which is convenient for the doctor to obtain. When the peristaltic parameter is displayed, the ultrasound image is displayed together.

In an embodiment shown in FIG. 3, the processor 20 controls the ultrasound probe 30 to transmit an ultrasound wave to the peristaltic object 10, and receive echoes of the ultrasound wave to obtain ultrasound echo data. The specific process is shown in step 11 to step 14.

Step 11: The processor 20 controls the ultrasound probe 30 to transmit a first ultrasound wave to the peristaltic object 10, and receive echoes of the first ultrasound wave to obtain first ultrasound echo data.

Step 12: The processor 20 obtains an ultrasound image of the peristaltic object 10 based on the first ultrasound echo data, for example, generates an ultrasound B-mode image reflecting a section of the endometrium based on the first ultrasound echo data. The specific process has been set forth in the foregoing description. Details are not described herein again. The processor 20 further displays the obtained ultrasound image in a display interface of the human-machine interaction apparatus 70.

Step 13: Determine a region of interest based on the ultrasound image. The region of interest may be a region selected by the user using the human-machine interaction apparatus 70, or may be a region identified by the processor 20, for example, an identified endometrial region. In other words, the region of interest may be determined in one of the following two manners. Manner 1: The human-machine interaction apparatus 70 receives a region selected by the user on the ultrasound image, and uses the selected region as the region of interest. The user may select the entire endometrial region, or may select only a part of the endometrium as the region of interest, which helps the user to perform targeted examination. Manner 2: The processor 20 performs image processing on the ultrasound image. For example, boundary recognition is performed by using an image segmentation technology to obtain the boundary of the endometrium. A region surrounded by the boundary of the endometrium is used as the region of interest.

Step 14: The processor 20 controls the ultrasound probe 30 to transmit a second ultrasound wave to a biological tissue corresponding to the region of interest, and receives echoes of the second ultrasound wave to obtain second ultrasound echo data. The ultrasound echo data of the region of interest is obtained for subsequent processing, which is more targeted. Moreover, a scanning parameter of the second ultrasound wave may be independent from the first ultrasound wave, and a higher imaging frame rate can be set to facilitate the subsequent peristalsis detection.

The detection of peristalsis is a dynamic detection process, and therefore the process of transmitting an ultrasound wave and receiving echoes needs to last for a specific period of time.

In this embodiment, the first ultrasound wave is used to generate the ultrasound image for display, while the second ultrasound wave is used for the subsequent peristalsis detection. The transmitting and receiving sequence of the second ultrasound wave is different from that of the first ultrasound wave, which means that at least one of the scanning parameters such as transmitting position, transmitting frequency, focus position, transmitting time interval, and transmitting range of the two ultrasound sequences is different. The scanning range is a region of interest to the user, and does not need to cover a region not of interest to the user. In order to obtain a finer motion status, a scanning frame rate of the second ultrasound wave may be set to be higher than that of the first ultrasound wave, or a detection direction different from that of imaging of the first ultrasound wave may be used.

In this case, in order to observe the ultrasound image synchronously during the peristalsis detection, the first ultrasound wave and the second ultrasound wave may also be transmitted alternately. Certainly, interpolation may also be performed in the time direction to obtain frame data at more moments.

In an optional embodiment, the first ultrasound wave and the second ultrasound wave may also be the same. In other words, the first ultrasound wave and the second ultrasound wave share the transmitting and receiving step, and the scanning parameters such as transmitting position, transmitting frequency, focus position, transmitting time interval, and transmitting range of the ultrasound sequences are all the same. This method is easy to implement, reduces a scanning time, and can generate an ultrasound image for the doctor to observe while obtaining a detection result of the peristalsis, which is convenient for the doctor to compare. For example, the ultrasound image is an ultrasound B-mode image. A frame of ultrasound B-mode image usually includes transmission and reception at a plurality of lateral positions in the field of view, and a series of ultrasound echo data frames can be obtained through repeated transmission. A series of ultrasound B-mode images can be obtained by B-mode data processing on the ultrasound echo data. By observing the ultrasound B-mode images, the doctor can see the position, shape, and movement of the endometrium. In addition, peristaltic wave detection processing is performed on the ultrasound echo data (refer to the embodiment shown in FIG. 2 for the process), and peristaltic parameters, such as the peristaltic displacement and the peristaltic velocity, of the endometrium at various moments can be obtained.

Step 2': Determine a peristaltic displacement or a peristaltic velocity of a point in the region of interest within a preset time length based on the second ultrasound echo data.

Step 3': Calculate a peristaltic parameter of the peristaltic object based on the peristaltic displacement or the peristaltic velocity of the point in the region of interest within the preset time length, where the peristaltic parameter is used to describe a motion status of peristalsis of the peristaltic object.

Step 4': Display the peristaltic parameter.

Step 2', step 3', and step 4' are the same as steps 2 to 4 in the embodiment shown in FIG. 2, and therefore are not described in detail.

In some embodiments of the disclosure, after the displacement (referred to as the peristaltic displacement) or velocity (referred to as the peristaltic velocity) of the peristaltic object (e.g., the endometrium) is obtained as in the foregoing embodiments, the obtained peristaltic displacement or peristalsis speed may be directly displayed, without further calculating the peristaltic parameter. In other words, the obtained peristaltic displacement or peristaltic velocity may be presented to the user in various suitable manners. For example, in an embodiment, a magnitude and/or direction of the peristaltic displacement may be displayed, or a magnitude and/or direction of the peristaltic velocity may be displayed. In an embodiment, alternatively, a graph of the peristaltic displacement or the peristaltic velocity as a function of time may be displayed. In an embodiment, alternatively, the peristaltic displacement or the peristaltic velocity may be mapped into different colors according to its size and/or direction and/or position and/or another nature, to obtain a color map, and the color map is displayed; and so on.

Those skilled in the art may understand that all or some of functions of various methods in the foregoing embodiments may be implemented through hardware or a computer program. When all or some of the functions in the above implementations are implemented by means of a computer program, the program may be stored in a computer-readable storage medium, and the storage medium may include: a read-only memory, a random access memory, a magnetic disk, an optical disk, a hard disk, and the like, and the program is executed by a computer to implement the above functions. For example, the program is stored in a memory of a device, and when the program in the memory is executed by a processor, all or some of the foregoing functions may be implemented. In addition, when all or some of the functions in the foregoing embodiments are implemented through a computer program, the program may alternatively be stored in a storage medium such as a server, another computer, a magnetic disk, an optical disc, a flash drive, or a removable hard disk, and downloaded or replicated for storage in a memory of a local device or version update is performed on a system of the local device. When a processor executes the program in the memory, all or some of the functions in the foregoing embodiments may be implemented.

Descriptions are provided herein with reference to various exemplary embodiments. However, those skilled in the art should understand that changes and corrections may be made to the exemplary embodiments without departing from the scope of this specification. For example, various operational steps and assemblies for executing the operational steps may be implemented in different methods on the basis of specific applications or in consideration of any number of cost functions associated with operations of the system (for example, one or more steps may be deleted, modified or incorporated into other steps).

In addition, those skilled in the art can understand that the principles herein may be reflected in a computer program product in a computer-readable storage medium, where the readable storage medium is loaded with computer-readable program codes in advance. Any tangible non-transitory computer-readable storage medium may be used, including a magnetic storage device (a hard disk, a floppy disk, or the like), an optical storage device (CD-ROM, DVD, Blu-ray disc, or the like), a flash memory, and/or the like. These computer program instructions may be loaded on a general-purpose computer, a special-purpose computer, or other programmable data processing devices to form a machine, such that these instructions, when executed on a computer or other programmable data processing apparatuses, may produce a means for implementing a specified function. These computer program instructions may alternatively be stored in a computer-readable memory. The computer-readable memory may instruct a computer or other programmable data processing devices to operate in a particular manner, such that the instructions stored in the computer-readable memory may produce an article of manufacture which includes a means for implementing a specified function. The computer program instructions may alternatively be loaded onto a computer or other programmable data processing devices to perform a series of operational steps on the computer or other programmable devices to produce a computer-implemented process, such that the instructions, when executed on the computer or other programmable devices, may provide steps for implementing a specified function.

Although the principles herein are shown in various embodiments, many modifications of structures, arrangements, proportions, elements, materials, and components particularly applicable to specific environmental and operating requirements may be made without departing from the principles and scope of the disclosure. These modifications and other changes or corrections fall within the scope of this specification.

The foregoing detailed descriptions are provided with reference to various embodiments. However, those skilled in the art should understand that various corrections and changes may be made without departing from the scope of the disclosure. Therefore, the disclosure is intended for an illustrative purpose other than a limitative purpose, and all these modifications fall within the scope of the disclosure. Similarly, the advantages, other advantages, and solutions to problems of the various embodiments are described above. However, the benefits, the advantages, the solutions to the problems, and any of their contributing factors, or solutions clarifying them should not be construed to be critical, necessary, or essential. The term "include" used herein and any other variations thereof all refer to a non-exclusive inclusion, such that a process, method, article, or device including a list of elements includes not only these elements, but also other elements that are not expressly listed or not inherent to the process, method, system, article, or device. In addition, the term "couple" used herein and any other variations thereof refer to a physical connection, an electrical connection, a magnetic connection, an optical connection, a communication connection, a functional connection, and/or any other connections.

Those skilled in the art should understand that many changes may be made to the details of the foregoing embodiments without departing from the basic principles of the disclosure. Therefore, the scope of the disclosure should be determined in accordance with the following claims.

What is claimed is:

1. A method for detecting endometrial peristalsis, applied to an ultrasound imaging device, wherein the ultrasound imaging device at least comprises an ultrasound probe, a processor and a human-machine interaction apparatus; and the method comprises:
   transmitting, by the ultrasound probe controlled by the processor, an ultrasound wave to an endometrium, and receiving, by the ultrasound probe controlled by the processor, echoes of the ultrasound wave to obtain ultrasound echo data;
   performing, by the processor, imaging on the ultrasound echo data to obtain an ultrasound image of the endometrium;

determining, by the processor, peristaltic displacements of points in the endometrium within a preset time length based on the ultrasound echo data,
wherein determining, by the processor, the peristaltic displacements of points in the endometrium within the preset time length based on the ultrasound echo data comprises:
selecting, from the ultrasound echo data, a first one-dimensional ultrasound echo data segment centered on a first point in the endometrium at a first moment, searching, in a one-dimensional search region covering the first point, a second one-dimensional ultrasound echo data segment at a second moment in a greatest correlation with the first one-dimensional ultrasound echo data segment, a position of a center point of the second one-dimensional ultrasound echo data segment being a position of the first point at the second moment, and obtaining a peristaltic displacement of the first point between the first moment and the second moment; and
obtaining, by analogy, the peristaltic displacements of the points in the endometrium at different moments within the preset time length;
calculating, by the processor, a peristaltic parameter of the endometrium based on the peristaltic displacements of the points in the endometrium within the preset time length, wherein the peristaltic parameter is used to describe a motion status of the endometrial peristalsis; and
displaying, by the human-machine interaction apparatus controlled by the processor, the peristaltic parameter.

2. The method of claim 1, wherein the peristaltic parameter comprises at least one of peristaltic amplitude of the endometrial peristalsis, a frequency of the endometrial peristalsis, total significant peristaltic movement time within the preset time length, a propagation direction of a peristaltic movement, a propagation speed of the peristaltic movement, a range of the peristaltic movement, a degree of disorder in the peristaltic movement, a degree of unevenness in the peristaltic amplitude, a degree of unevenness in a peristaltic direction, and a distribution of the peristaltic movement in the endometrium.

3. The method of claim 1, wherein the preset time length is greater than or equal to a period of the endometrial peristalsis.

4. The method of claim 1, wherein the peristaltic parameter comprises at least one of a tissue strain caused by the endometrial peristalsis, a tissue strain rate caused by the endometrial peristalsis, and an acceleration of a peristaltic movement.

5. The method of claim 1, wherein the peristaltic parameter comprises-statistical quantity of the peristaltic displacements.

6. The method of claim 1, wherein calculating the peristaltic parameter of the endometrium based on the peristaltic displacements of the points in the endometrium within the preset time length comprises:
generating a relationship curve of the peristaltic displacements versus time based on the peristaltic displacements of the points in the endometrium within the preset time length; and
calculating at least one of an amplitude of the endometrial peristalsis, a frequency of the endometrial peristalsis, and total significant movement time within the preset time length based on the relationship curve.

7. The method of claim 1, wherein calculating the peristaltic parameter of the endometrium based on the peristaltic displacements of the points in the endometrium within the preset time length comprises:
calculating motion parameters of the points in the endometrium based on the peristaltic displacements of the points in the endometrium within the preset time length, the motion parameter comprising at least one of a maximum peristaltic displacement, a minimum peristaltic displacement, an average peristaltic displacement, and total significant movement time; and
obtaining a propagation direction of the endometrial peristalsis according to an order in which the points in the endometrium reach a preset motion parameter.

8. The method of claim 7, wherein after the propagation direction of the endometrial peristalsis is obtained, the method further comprises:
obtaining a propagation speed of the endometrial peristalsis based on a distance between at least two points in the propagation direction and a time difference between moments at which the two points reach the preset motion parameter.

9. The method of claim 7, wherein after the motion parameters of the points in the endometrium are calculated, the method further comprises:
determining whether the motion parameters of the points in the endometrium exceed a preset parameter threshold; and
using a region formed by points with the motion parameters exceeding the preset parameter threshold as a range of a peristaltic movement of the endometrium.

10. The method of claim 1, wherein displaying the peristaltic parameter comprises: displaying a relationship curve of the peristaltic parameter versus time.

11. An ultrasound imaging device, comprising:
an ultrasound probe configured to transmit an ultrasound wave to a region of interest in a biological tissue, and receive echoes of the ultrasound wave;
a transmitter/receiver circuit configured to control the ultrasound probe to transmit a first ultrasound wave to an endometrium, and receive echoes of the first ultrasound wave to obtain ultrasound echo data;
a human-machine interaction apparatus configured to receive a user's input and output visual information; and
a processor configured to:
obtain an ultrasound image of the endometrium based on the ultrasound echo data;
determine peristaltic displacements of points in the endometrium within a preset time length based on the ultrasound echo data, by
selecting, from the ultrasound echo data, a first one-dimensional ultrasound echo data segment centered on a first point in the endometrium at a first moment,
searching, in a one-dimensional search region covering the first point, a second one-dimensional ultrasound echo data segment at a second moment in a greatest correlation with the first one-dimensional ultrasound echo data segment, wherein a position of a center point of the second one-dimensional ultrasound echo data segment is a position of the first point at the second moment,
obtaining a peristaltic displacement of the first point between the first moment and the second moment, and obtaining, by analogy, the peristaltic displacements of the points in the endometrium at different moments within the preset time length;

calculate a peristaltic parameter of the endometrium based on the peristaltic displacements of the points in the endometrium within the preset time length, wherein the peristaltic parameter is used to describe a motion status of endometrial peristalsis; and display the peristaltic parameter using the human-machine interaction apparatus.

12. The ultrasound imaging device of claim 11, wherein the peristaltic parameter comprises at least one of amplitude, frequency, total significant movement time within the preset time length, propagation direction, propagation speed, and peristalsis range of the endometrial peristalsis.

13. The ultrasound imaging device of claim 11, wherein the preset time length is greater than or equal to a period of the endometrial peristalsis.

14. The ultrasound imaging device of claim 11, wherein the processor calculating a peristaltic parameter of the endometrium based on the peristaltic displacements of the points in the endometrium within the preset time length comprises:

generating a relationship curve of the peristaltic displacements versus time based on the peristaltic displacements within the preset time length; and calculating at least one of an amplitude of the endometrial peristalsis, a frequency of the endometrial peristalsis, and total significant movement time within the preset time length based on the relationship curve;

or calculating motion parameters of the points in the endometrium based on the peristaltic displacements of the points in the endometrium within the preset time length, the motion parameter comprising at least one of a maximum peristaltic displacement, a minimum peristaltic displacement, an average peristaltic displacement, and total significant movement time; and obtaining a propagation direction of the endometrial peristalsis according to an order in which the points in the endometrium reach a preset motion parameter.

* * * * *